United States Patent [19]
Debenedetti et al.

[11] Patent Number: 6,063,910
[45] Date of Patent: May 16, 2000

[54] PREPARATION OF PROTEIN MICROPARTICLES BY SUPERCRITICAL FLUID PRECIPITATION

[75] Inventors: Pablo G. Debenedetti, Princeton, N.J.; Gio-Bin Lim, Seoul, Rep. of Korea; Robert K. Prud'Homme, Princeton Junction, N.J.

[73] Assignee: The Trustees of Princeton University, Princeton, N.J.

[21] Appl. No.: 07/792,292

[22] Filed: Nov. 14, 1991

[51] Int. Cl.[7] .................................................. A61K 9/14
[52] U.S. Cl. .......................... 530/418; 424/44; 424/45; 424/489; 264/5; 426/425; 514/2; 530/350
[58] Field of Search .................. 422/1; 426/241, 426/312, 425, 615; 530/418, 350; 424/44, 45; 264/5; 514/2

[56] References Cited

U.S. PATENT DOCUMENTS

| | | | |
|---|---|---|---|
| 3,773,919 | 11/1973 | Boswell | 424/19 |
| 4,263,253 | 4/1981 | Pilz | 422/1 |
| 4,985,270 | 1/1991 | Singer | 426/515 |
| 4,990,355 | 2/1991 | Gupta | 426/602 |
| 5,013,713 | 5/1991 | Mitchell | 514/2 |
| 5,043,280 | 8/1991 | Fischer | 435/235.1 |
| 5,169,968 | 12/1992 | Rice | 554/193 |
| 5,301,664 | 4/1994 | Sievers | 128/200.23 |
| 5,639,441 | 6/1997 | Sievers | 424/9.3 |
| 5,814,678 | 9/1998 | Randolph | 522/18 |
| 5,851,453 | 12/1998 | Hanna | 264/5 |
| 5,904,935 | 5/1999 | Eckenhoff | 424/489 |

FOREIGN PATENT DOCUMENTS

WO9003782  4/1990  WIPO.

OTHER PUBLICATIONS

CA 111:216768. (1989).

Tom & Debenedetti, Formation of Bioerodible Polymeric Microspheres and Microparticles by Rapid Expansion of Supercritical Solutions, Dept of Chemical Engineering, Princeton University, 1991.

Chang & Randolph, Solvent Expansion and Solute Solubility Predictions in Gas–Expanded Liquids, AICHE Journal, Jun. 1990, vol. 36, No. 6, pp. 939–942.

Tavana AICHE Journal 35, 1625–1630, 1989.

Tom, J. Aerosol Sci 22, 555–584 1991.

*Primary Examiner*—Michael P. Woodward
*Assistant Examiner*—David Lukton
*Attorney, Agent, or Firm*—Mathews, Collins, Shepherd and Gould, P.A.

[57] ABSTRACT

The present invention comprises passing a solution of a soluble material, preferably a protein, in a solvent through a continuum of supercritical antisolvent fluid and precipitating the soluble material. This can be conducted by passing the solution through the continuum of supercritical fluid in the form of droplets, which can be sprayed through the supercritical fluid. The plurality of droplets can be passed cocurrently or countercurrently with respect to a stream of antisolvent fluid. Alternatively, the solution can be passed through the continuum of supercritical antisolvent fluid in the form of a thin film or a plurality of fine streams.

9 Claims, 4 Drawing Sheets

PREPARATION OF PROTEIN MICROPARTICLES BY SUPERCRITICAL FLUID PRECIPITATION

BACKGROUND OF THE INVENTION

The present invention relates to a method and composition to form protein microparticles; more particularly, the present invention relates to method of forming microparticles using fluid antisolvent precipitation and compositions including such proteins.

DESCRIPTION OF RELATED ART

Conventional means of administering drugs (e.g., pills and tablets) provide a single burst of drug in the blood. This initial spike is followed by a decay in blood concentration. Because every drug has a range of concentration below which its therapeutic effect is limited, and above which toxic side effects occur, it is desirable to release the drug at a controlled rate and minimize fluctuations. In controlled release, this is achieved by incorporating a rate-limiting step into the design of the delivery system. Among the many types of controlled release systems there are bioerodible polymer microspheres in the range of 1 to 50 micrometers ($\mu$m). Such small microspheres can be injected subcutaneously or intramuscularly. Bioerodible polymers are materials that are degraded by body fluids to non-toxic products. The polymer particles contain the drug of interest in dispersed form. Drug release occurs partly as a result of polymer degradation inside the body. Systems aimed at providing spatial or temporal control of drug release in the body are referred to generically as controlled drug delivery devices.

Controlled release of proteins, such as therapeutic enzymes, requires the formation of small particles that can be uniformly dispersed in the polymer matrix. Techniques to produce protein particles include spray drying, lyophilization, milling, grinding, and protein micronisation, WO/90/132. Only the last method leads to small particles.

Jean W. Tom and Pablo G. Debenedetti, *Formation of Bioerodible Microspheres and Microparticles by Rapid Expansion of Supercritical Solutions,* Department of Chemical Engineering, Princeton University, 1991, disclose a process to make biocompatible and bioerodible polymer microspheres, mainly polyhydroxy acids including, poly(L-lactic acid) (L-PLA), poly(D,L-lactic acid), (DL-PLA) and poly(glycolic acid) (PGA). Microparticles and microspheres of these polymers were made with the goal of being used for controlled delivery of pharmaceuticals. Nucleation of poly (L-lactic acid) from $CO_2$ and $CO_2$-acetone mixtures produced microparticles and microspheres ranging from 4 to 25 micrometers $\mu$m. Microspheres (2–20 $\mu$gm) were also obtained with chlorotrifluoromethane as a solvent.

The technique to produce the microspheres and microparticles used by Tom and Debenedetti was to apply rapid expansion of supercritical solutions. This was known from Matson et al., *Expansion of Supercritical Fluid Solutions: Solute Formation of Powders, Thin Films and Fibers.* Ind. Eng. Chem. Res. 1987 26, 2298–2306. In the disclosed process of rapid expansion of supercritical solutions, a nonvolatile solute is dissolved in a supercritical fluid. The resulting solution is highly compressible in the vicinity of the solvents critical point. Nucleation of the solute is triggered mechanically by reducing the solution's density, through a rapid expansion, and therefore reducing its dissolving capacity; Kumar and Johnston, *Modelling the Solubility of Solids in Supercritical Fluids with Density as the Independent Variable,* J. Supercrit. Fluids. 1988, 1, 15–22. In this process a combination of a rapidly propagating mechanical perturbation and high supersaturation ratios leads to uniform conditions within the carrier fluid and hence, in principle, to narrow particle size distributions into small particles.

Chang and Randolph, *Solvent Expansion and Solute Solubility Predictions in Gas-Expanded Liquids,* AIChE Journal, June 1990, Vol. 36, No. 6, pp 939–942 disclose using gas antisolvent addition for liquid phase precipitation of solids. This process was also disclosed by Gallagher et al., *Gas (Gas Anti-Solvent) Recrystallization: A New Process to Recrystallize Compounds Insoluble in Supercritical Fluids,* Am. Chem. Soc. Symp. Ser., No. 406 (1989).

Chang et al. disclose recrystallization of organics using the gas antisolvent process. In particular, there is disclosed the recrystallization of acetaminophen from a solution of butanol using $CO_2$. $\beta$-carotene was recrystallized from toluene also using $CO_2$. In accordance with the disclosed process $CO_2$ was charged to the top of the column or reservoir containing the solution to be gas expanded.

SUMMARY OF THE INVENTION

The present invention relates to a method for the formation of microparticles, particularly protein microparticles, from a solution by antisolvent recrystallization using a supercritical fluid. In accordance with the present invention, a solution of protein is formed in a solvent. A supercritical antisolvent fluid is dissolved in the solution at a controlled rate to expand the solution and precipitate the protein.

The present invention is particularly useful wherein the protein is a hydrophobic enzyme, (i.e., one that can be dissolved in a predominantly non-aqueous solvent). Preferred proteins are selected from the group consisting of insulin, catalase, adrenocorticotrophin hormone and peroxidase. Preferred solvents for the protein are non-aqueous solvents selected from the group consisting of ethanol, dimethylsulfoxide, tetrahydrofuran, acetic acid, formamide, dimethylformamide, ethylene glycol, liquid polyethylene glycol, and N, N-dimethylanine. Preferred antisolvent fluids are selected from the group consisting of carbon dioxide, ethane, ethylene, sulfur hexafluoride, nitrous oxide, chlorotrifluoromethane and monofluoromethane.

A preferred method of the present invention comprises passing the solution of a soluble material in a solvent through a continuum of supercritical antisolvent fluid and precipitating the soluble material. This can be conducted by passing the solution through the continuum of supercritical fluid in the form of droplets, which can be sprayed through the supercritical fluid. The plurality of droplets can be passed cocurrently or countercurrently with respect to a stream of antisolvent fluid. Most preferably, the droplets are passed cocurrently. Alternatively, the solution can be passed through the continuum of supercritical antisolvent fluid in the form of a thin film or a plurality of fine streams.

In accordance with the method of the present invention, particularly by the use of a continuum phase of supercritical antisolvent fluid, the liquid solution rapidly expands, causing the soluble material to precipitate out very rapidly. This results in extremely uniform and fine particle sizes.

In accordance with the present invention, the soluble material, preferably protein, can be made having a particle size wherein the precipitated material has a particle size of less than 10, preferably less than 5, more preferably less than 3, and most preferably less than 1 micrometer in equivalent diameter. Equivalent diameter is defined as the diameter of a sphere having the same volume as the particle would have an equivalent diameter as indicated. Where the soluble material is globular, such as globular protein, the equivalent diameter is preferably less than 3 micrometers, and more preferably less than 1 micrometer. Wherein the soluble material precipitates out in a needle-like configuration, the average diameter of the needle is preferably less than 2 and more preferably less than 1 micrometer, and the length of the particle is less than 5 and preferably less than 3 micrometers. Typically, the particles of the present invention have a uniform and relatively narrow particle distribution.

The present invention also includes a plurality of protein particles wherein substantially all of the protein particles have an equivalent diameter of less than 5, preferably less than 3, and most preferably less than 1 micrometers. Additionally, the protein particles preferably have a narrow size distribution.

The small and relatively uniform distribution of proteins artificially formed according to the present invention have a chemically uniform composition. Where more than one particle is made the blend is a controlled blend of two or more, preferably two or three different materials in controlled amounts and sizes.

The small particulate material of the present invention is particularly useful in the preparation of devices that provide control of the rate of drug release. Such compositions comprise a bioerodible polymer and a plurality of very small active ingredients, such as proteins. The small size of the particles is important to insure a uniform dispersion within the polymeric matrix. It is important that the polymer particles be small (<50 $\mu$m) so that they can be injected. The method of the present invention and proteins described in the present invention are therefore particularly useful in such formulations. Formulations of particular importance are those made using a bioerodible polymeric matrix and at least one protein having an equivalent diameter of less than about 3 micrometers. Preferred polymers are polyhydroxy acids such as poly(L-lactic acid), poly(D,L-lactic acid) and poly (glycolic acid). The preferred composition comprises from 0.1 to 50 weight percent of protein and a corresponding amount of polymer matrix.

BRIEF DESCRIPTION OF THE DRAWINGS

In FIG. 1 "V" represents valves, "P1" represents pressure sensors, "T1" represents temperature sensors. In the key, reference characters are back pressure regulator 1, rotameter 2, filter 3, check valve 4, metering valve 5, shut-off valve 6, rupture disc 7, and heat exchanger 8.

DESCRIPTION OF THE PREFERRED EMBODIMENTS

Figure 1:
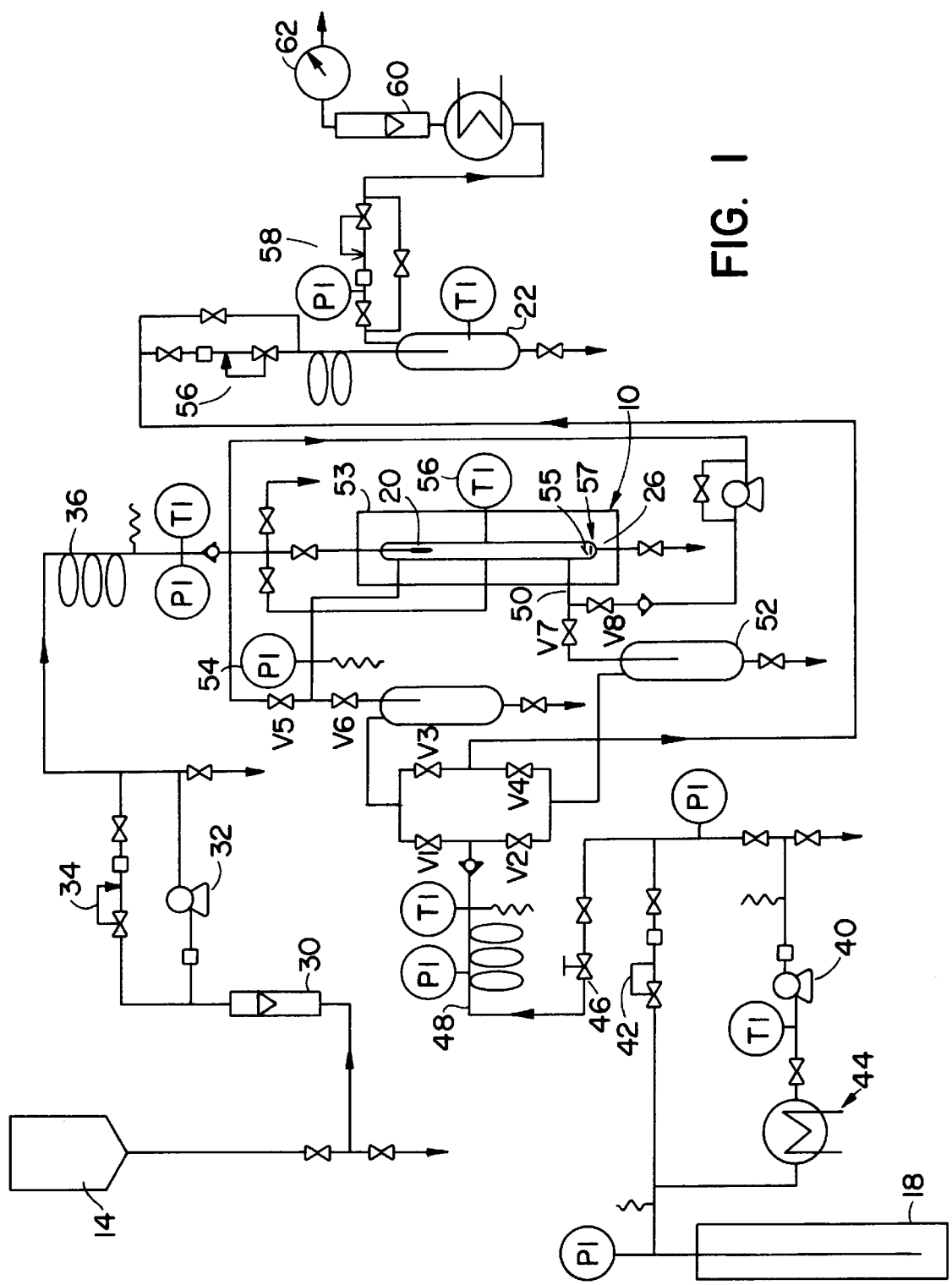
FIG. 1 is a schematic drawing of an experimental apparatus for the antisolvent recrystallization and liquid expansion useful in the present invention.

The present invention will be understood by those skilled in the art by reference to FIG. 1 which is a schematic diagram of an experimental apparatus of the antisolvent recrystallization and liquid expansion experiments to be described later. It will be appreciated by those skilled in the art that this experimental process can be scaled up to pilot plant and commercial size.

The system of the present invention comprises a crystallizer 10 to which a solution of dissolved material is fed, preferably a protein solution from a protein solution source 14. A supercritical fluid to be used as an antisolvent is fed to crystallizer 10 from antisolvent source, such as antisolvent gas tank 18. In accordance with the present invention, the antisolvent gas source is brought to supercritical conditions by suitable means and is fed to crystallizer 10. The supercritical fluid is the continuum phase in crystallizer chamber 20 within crystallizer 10. The solution of soluble material, preferably protein, passes through the continuum of the supercritical antisolvent supercritical fluid within crystallizer chamber 20.

In the crystallizer the supercritical antisolvent supercritical fluid dissolves in the solution at a controlled rate. The solution expands and the soluble material, protein, precipitates out. The depleted solution and spent supercritical antisolvent supercritical fluid are fed to a depressurization means, such as depressurization tank 22 to be brought back to ambient conditions. The precipitated crystals can be collected from the crystallizer 10 at crystal collection port 26. The crystals can be collected by any suitable means, such as on a filter or on a glass plate.

FIG. 1 illustrates a specific and preferred experimental system to controllably precipitate a soluble material, preferably a protein. Protein solution can be prepared or stored in protein solution source 14. The protein solution is fed from protein solution source 14 to crystallizer 10 through suitable flow measuring means, such as protein rotameter 30 and through a high pressure liquid pump 32. The pressure can be controlled using a back-pressure regulator 34. The pressurized protein solution is fed to crystallizer chamber 20. Preferably, it is injected into the top of the crystallizer through a laser-drilled platinum disc. This results in a fine spray of protein solution droplets into the crystallizer chamber 20. Preferably, the disc has at least one orifice to cause a fine spray. A typical orifice is from 5 to 50 and preferably from 10 to 30 and most preferably from 15 to 20 micrometers in diameter. The protein solution can be brought to the desired temperature by a suitable heating means, such as coils 36, which are kept at the desired temperature by circulating air. Heating can be provided by strip heaters and forced circulation of air.

An antisolvent fluid, such as carbon dioxide, is fed from antisolvent tank 18 to an antisolvent compression pump 40. The pressure can be controlled by a back-pressure regulator 42. Excess solvent in the stream can recycle back to the liquid inlet side of the pump 40. There can be a suitable antisolvent heat exchanger 44 between the antisolvent tank and the antisolvent compression pump 40 to condense the antisolvent fluid. The compressed antisolvent is fed through suitable micrometering means, such as micrometering valve 46. Optionally, there can be additional thermostating means such as coils 48 between solvent pump 40 and crystallizer 10. The supercritical antisolvent fluid is fed to crystallizer chamber 20. Crystallizer chamber 20 thereby contains a continuum of supercritical fluid.

In crystallizer chamber 20 the supercritical antisolvent fluid dissolves in the protein solution at a controlled rate depending on the stream or droplet geometry, temperature and concentration. As solution expands, the soluble material, preferably protein, precipitates out. Use of a continuum of supercritical fluid and passage of a fine stream, film, or droplets through the supercritical fluid results in rapid expansion of the liquid solution and precipitation of the dissolved protein. This results in immediate precipitation of extremely fine particles less than 10 micrometers in equivalent diameter and preferably less than 5, more preferably less than 3, and most preferably less than 1 micrometer in diameter, particularly for soluble material which precipitates out in a globular shape. Needle-like precipitates have a diameter of less than about 3 and more preferably less than 1 micrometer with a length of less than 5, and preferably less than 3 micrometers. The rapid precipitation results in a narrow particle distribution as exemplified and shown in FIGS. 2 to 7. The precipitated particles fall to the bottom of the crystallizer and are deposited on suitable collection means, such as a filter, or on an inclined glass slide in experimental size equipment at crystallizer collector 26.

A fluid mixture of spent solvent and supercritical fluid can be collected from the bottom of the crystallizer chamber 20 through line 50. The fluid mixture passes through valve V7 to collection tank 52 through valve V4 to depressurization tank 22 where the mixture is depressurized and expanded to atmospheric pressure. The system should be sized to handle protein solutions at pressures up to 6000 psi, and preferably in the range of from atmospheric pressure to 6,000 psi from temperatures ranging from 20° C. to 60° C. and preferably 30° C. to 50° C.

The antisolvent tank 18 can supply an antisolvent, preferably in liquid form, at a temperature range of from 10 to 40° C. and preferably from 20 to 30° C., such as liquid carbon dioxide at 25° C. The antisolvent is cooled in heat exchanger 44. Solvent pump 40 brings the liquid antisolvent to supercritical pressure. Typical conditions at the outlet of pump 40 are from 25 to 45° C. and more preferably from 30 to 40° C., and 60 to 200 atmosphere pressure, more preferably 100 to 150 atmosphere pressure.

Different flow patterns can be used in crystallizer 10. The direction of antisolvent supercritical fluid flow in the crystallizer (upward or downward) can be determined by the valves before and after the crystallizer. For upward flow in the crystallizer, valve V2 and valve V3 are open, and valve V1 and valve V4 are closed. Where the antisolvent fluid is to flow downward the valves are reversed. The flow of protein solution can be cocurrent or countercurrent to the flow of antisolvent fluid. In the preferred embodiment with continuous operation, protein solution is pumped into the crystallizer by high pressure liquid pump 32 and its instantaneous flow rate is measured by the liquid rotameter 30. The pressure is controlled using a back-pressure regulator 34 and pressurized protein solution is injected into the top of the crystallizer. The antisolvent fluid, preferably carbon dioxide at supercritical conditions, is also injected into the top of the crystallizer for cocurrent flow of both the supercritical solvent fluid continuum through the crystallizer and the protein solution through the crystallizer, both from top to bottom. The crystallizer can be operated in batch, semi-batch or continuous operation.

In accordance with the method of the present invention, a solution of a soluble material, preferably a protein in a solvent, is passed through a continuum of the supercritical antisolvent fluid and the soluble material precipitated. The solution of soluble material can be passed through cocurrently or countercurrently in relation to a continuum stream of antisolvent supercritical fluid. The solution is preferably in a form having a relatively large surface area for immediate exposure to the supercritical fluid. This can be accomplished by a suitable orifice means 53, such as a disc having at least one hole or slot. Preferably the solution is in the form of a plurality of droplets having a diameter of from 10 to 500 $\mu$m or at least one continuous fine stream having a diameter of less than 1 millimeter, or a thin film having a thickness of less than 1 millimeter. The conditions for precipitation are chosen to result in rapid expansion of the liquid solution by the antisolvent fluid and precipitation of fine particles of the soluble material.

Preferred soluble material are protein, such as hydrophobic enzymes, which can be selected from the group consisting of insulin, catalase, adrenocorticotrophin hormone and peroxidase.

Useful solutions for the protein comprise at least one non-aqueous solvent selected from the group consisting of ethanol, formamide, dimethylsulfoxide, tetrahydrofuran, acetic acid, dimethylformamide, ethylene glycol, liquid polyethylene glycol and dimethylaniline.

Useful supercritical fluids with critical temperatures (° C.) and critical pressures (atm) include ethane (32.2° C., 48.1 atm), ethylene (9.21° C., 39.7 atm); sulfur hexafluoride (45.5° C., 37.1 atm), nitrous oxide (36.5° C., 71.7 atm) chlorotrifluoromethane (28° C., 38.7 atm), and monofluoromethane (44.5° C., 58 atm). A solution of water and ethanol has been used. However, the presence of water in such solutions has been found to lower the production of small particle protein.

In accordance with the present invention there is obtained a protein composition having protein particles wherein substantially all of the protein particles are isolated and have an equivalent diameter of less than 5, more preferably less than 3, and most preferably less than 1 micrometer. The protein composition has a narrow particle distribution shown in FIGS. 2–7. These proteins, which are isolated, have uniform or controlled chemical compositions. Therefore, samples of a composition consisting essentially of a desired protein can be isolated and made.

The isolated proteins of the present invention can be used to make temporal drug release compositions. Such compositions can comprise a bioerodible polymeric matrix and at least one protein having an equivalent diameter of less than 3 micrometers. Preferred polymers are polyhydroxy acids such as those selected from the group consisting of poly(L-lactic acid), poly(D,L-lactic acid) and poly(glycolic acid). The composition can comprise for 0.1 to 50 weight percent of the protein.

Preferably the drug release compositions contain a polymer matrix having a continuum of bioerodible polymer matrix with the protein particles dispersed therewith. Such particles can be made by means known in the art as discussed in the Background of the Invention.

Following are several Examples which illustrate the nature of the invention and the manner of carrying it out. Although the following Examples were conducted in an experimental laboratory setup, the method of the present invention can be scaled up to pilot and commercial size and operation. The method can be used in batch, semi-batch and continuous operation. The invention should therefore not be limited to the details of these Examples.

Referring to FIG. 1, the following equipment was used in the setup. In the experiments that follow liquid carbon dioxide in solvent tank 18 was compressed by high pressure liquid pump 40 which was an American Lewa Plunger Metering Pump, Model EL-1; rated at 6,000 psi and 2 gallons per hour. The pressure was controlled by a back-pressure regulator 42 which was a Tescom, Model 54-2100 Series, rated at 6,000 psi. The compressed carbon dioxide was introduced into a see-through crystallizer 20 which was a Jerguson Gauge, Model 19T40, 316 stainless steel 5,000 psi, 1.3 centimeter by 1.3 centimeter, 31.8 centimeter long, 50 cubic centimeter through micrometering valve 46 which was an Autoclave Engineering Micrometering Valve 60VRMM. The pressurized carbon dioxide was preheated in coiled tubes 48.

The pressure in the crystallizer was indicated by a crystallizer pressure gauge 54 which was a Bourdon Gauge, Omega Model PGJ-45B-5000, rated at 5000 psi, and controlled by back-pressure regulator 50 which was a Tescom 26-1700 Series, rated at 6,000 psi.

The protein solution from protein solution tank 14 was pumped in continuous operation by a high pressure pump which was a Milton Roy LDC Duplex Metering Pump. The instantaneous flow was measured by liquid rotameter 30 which was a Fischer and Porter; Model 10A6132, 0–14 cubic centimeters per minute of water flow. The pressure of the protein solution was controlled using a back-pressure regulator 34 which was a Tescom; 26-1700 Series, 10,000 psi rated regulator. The protein solution was preheated in coiled tubes 36.

The pressurized protein solution was injected into the top of the crystallizer 10 through a laser-drilled platinum disc 53, Ted Pella; 3 mm OD×0.24 mm thick; 20 micrometers in diameter.

At the bottom of the crystallizer the protein particles were precipitated and deposited on an inclined glass slide after crystallization. The plane of the glass slide 55 was at a 10° angle to the direction of the protein solution flow. Additionally, a filter 57, Mott Metallurgical; 316 Stainless Steel 1.6 centimeters in diameter, 0.5–2 micrometer pore size was located below the glass slide to collect all the protein particles. A thermocouple 56, Omega Engineering Type J, was placed in the middle of the crystallizer to monitor the temperature.

Protein particles collected on the glass slides were examined through a Carl Zeiss Universal Optical Microscope and a Scanning Electron Microscopy JEOL JSM-840A, with samples coated with gold-palladium. The particles on the microfilter were also examined with the Scanning Electron Microscope.

The fluid mixture of carbon dioxide, ethanol and water coming out of the crystallizer was depressurized and expanded to atmospheric pressure by passing through a cylindrical depressurizing tank 22, Swagelok, 150 ml, 5,000 psi and back-pressure regulator 58, Tescom, 26-1700 Series, rated at 6,000 psi.

The instantaneous and total flow rates of solute free $CO_2$ gas were measured with rotameter 60 (Fischer and Porter; Model 10A4555, 0–3.35 SCFM AIR and dry test meter 62, American Meter; Model DTM200A, respectively.

During the experiment the normal flow rates of protein solution and antisolvent fluid were 0.35 $cm^3$/min and 35g/min, respectively, and typical operating time was 4 hours for continuous operation. The whole system was enclosed in an air chamber where temperature was controlled using a PID temperature controller, Omega Engineering Model CN9000, and strip heaters.

To measure the expansion behavior of $CO_2$-ethanol solution, 20 mls of ethanol solution was preloaded into the crystallizer and pressure was increased by 200 psi increments through valves V2 and V7. Fluid solvent was then circulated through valve V8, crystallizer 20 and valve V5 using a high pressure compressor (Haskell; Double Acting Single Stage Model ACD-62) with closed valves V6 and V7 until the system reached the equilibrium state and the liquid level remained constant.

EXAMPLE 1

Catalase particles, FIGS. 2–5, were made having and equivalent diameter of less than 1 μm.

Liquid solution was used which had 20 mg catalase (from bovine liver) [Sigma Chemicals C-40] in 200 ml of 90% ethanol (Pharmco Products Co., 200 proof)–10% water (deionized through a reverse osmosis apparatus, Hydro Picosystem). The solution pH was adjusted to 3.22 with HCl.

Liquid carbon dioxide (MG industries; Bone-dry grade, >99.8%) was compressed by a high pressure liquid pump 40. The delivery pressure (1600 psi) was controlled by a back-pressure regulator 42. The pressurized liquid was pre-heated to a supercritical temperature (35° C.) and flowed through coiled tube 48 before entering the crystallizer 10. The system was enclosed and thermostating was achieved by circulating hot air under temperature control (Omega Engineering Model CN9000), with heating provided by strip heaters. The see-through crystallizer chamber 20 was kept at 35° C.

The supercritical fluid was fed to the crystallizer through a micrometering valve 46, with valves V1 and V4 open; and V2 and V3 closed. The pressure inside the crystallizer was kept at 1300 psi by back-pressure regulator 56. The instantaneous and total flow rates of supercritical fluid were measured with rotameter 60 and dry test meter 62, respectively. The flow rate of the supercritical fluid was 33 g/min.

The liquid solution containing the enzyme was pressurized and circulated by liquid pump 32 and back-pressure regulator control (1430–1530 psi). The solution circulated through coil 36 and was preheated to 35° C. It entered the top of the crystallizer through a laser-drilled platinum disc (Ted Pella: 3 mm OD×0.24 mm thick; 20 μm), and emerged as very small droplets. The liquid flow rate was 0.35 cc/min. The liquid and supercritical streams circulated cocurrently downwards.

The fluid mixture of carbon dioxide, ethanol and water exiting the crystallizer was depressurized and expanded to atmospheric pressure by flowing through cylindrical depressurizing tank 22, and back-pressure regulator 58.

Figure 2:
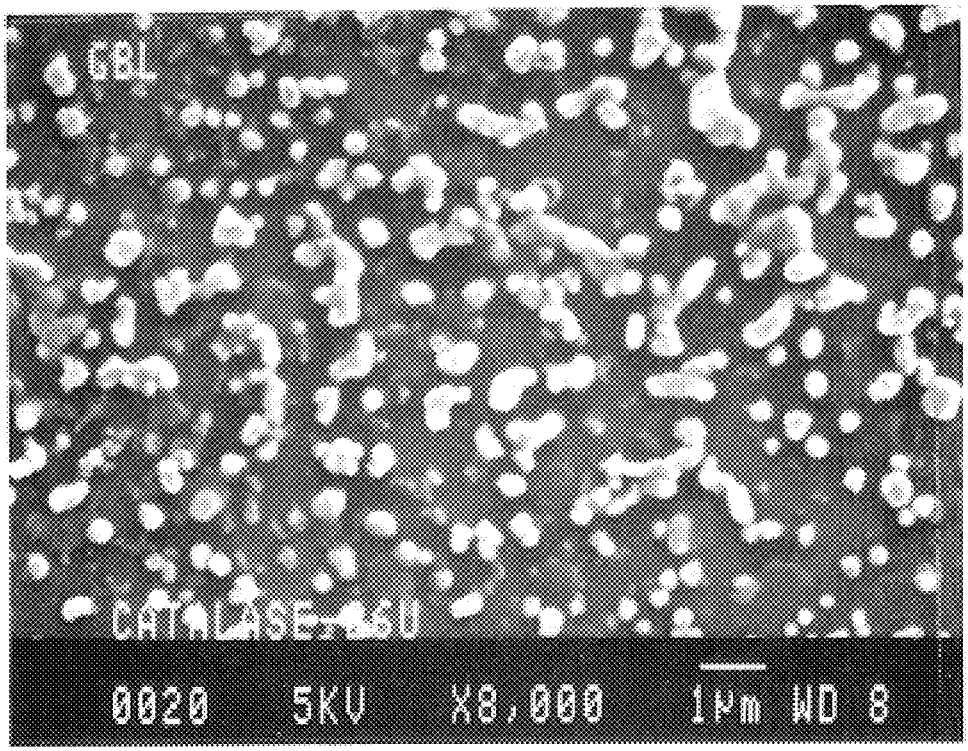
FIG. 2 is a microphotograph magnified 8,000 times showing catalase particles made in Example 1 the particles collected on the glass slides upside.
Figure 3:
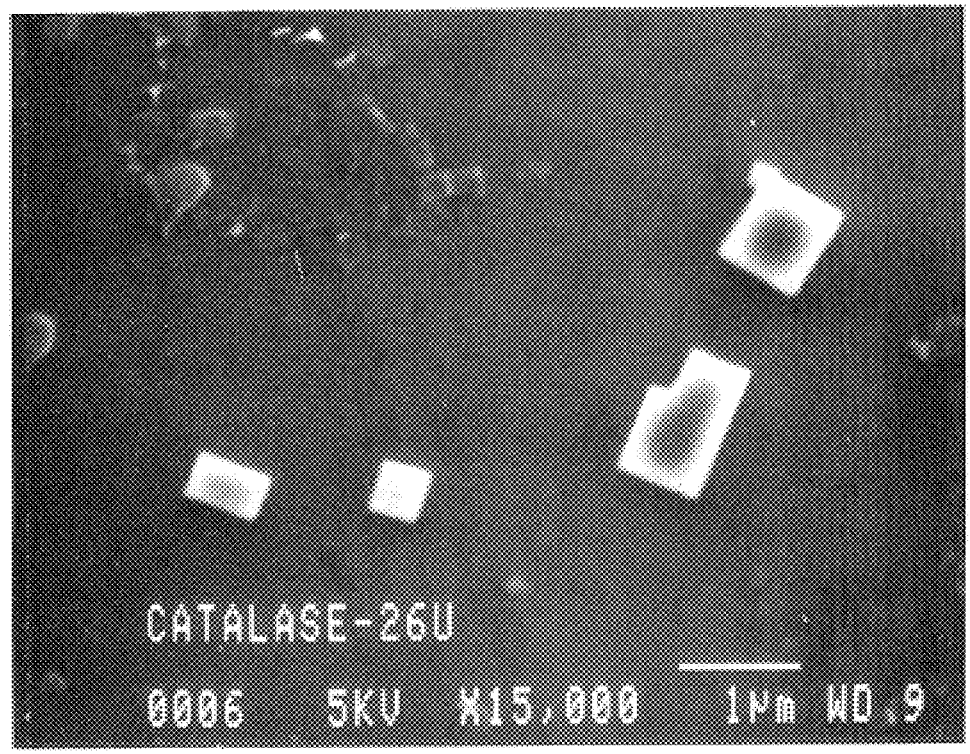
FIG. 3 is a microphotograph of the same material as in FIG. 2 having a magnification of 15,000.
Figure 4:
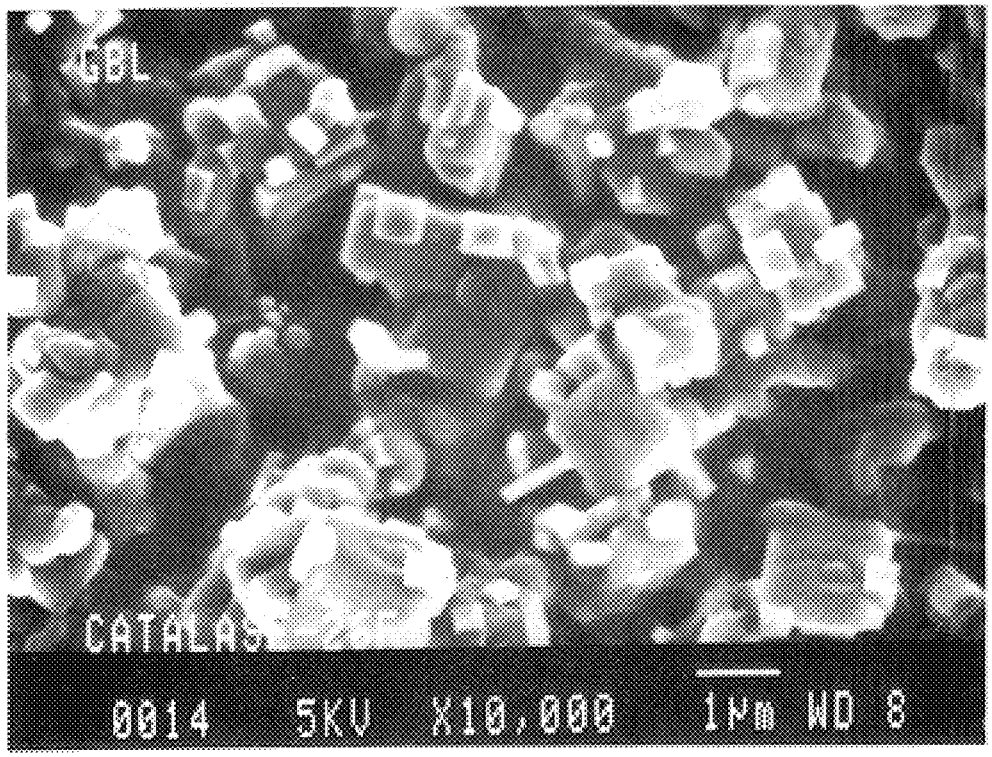
FIG. 4 is a microphotograph of the same material as in FIG. 3 where the particles are collected on a filter and magnified 10,000 times.
Figure 5:
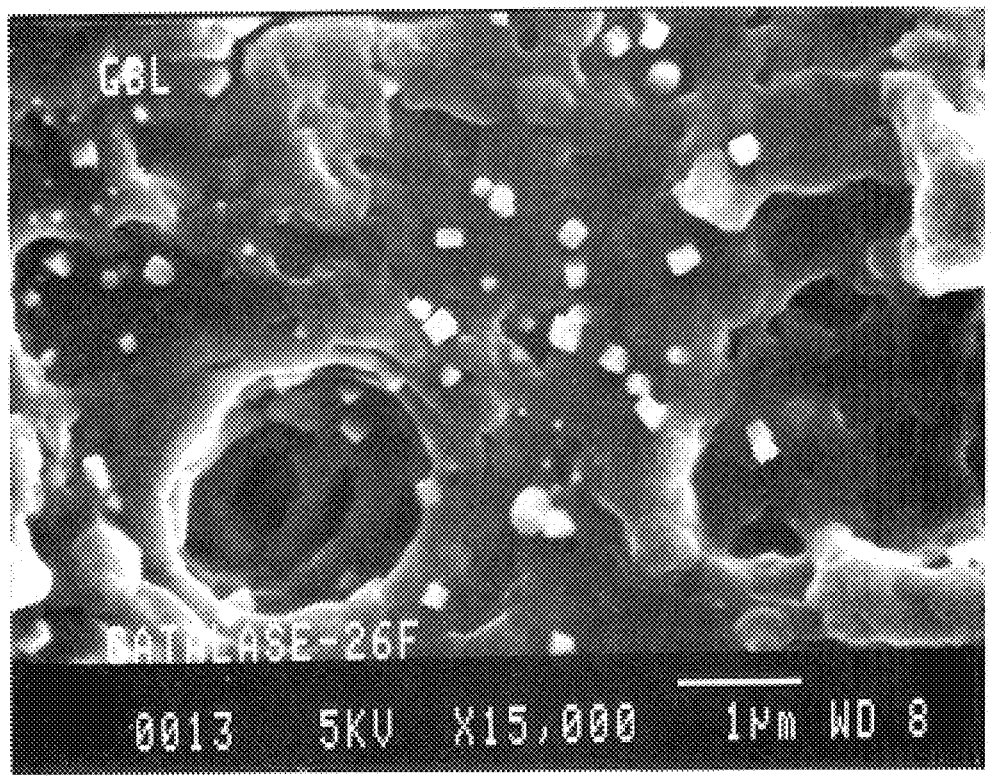
FIG. 5 is a microphotograph as recited in FIG. 4 magnified 15,000 times.

The supercritical fluid expanded and eventually dissolved most of the liquid solvent, causing the enzyme particles to precipitate. The particles were collected on an inclined glass slide located at the bottom of the crystallizer, forming an angle of approximately 10° to the direction of the protein solution's flow. Particles were also collected on a filter (Mott Metallurgical; 316 Stainless Steel, 1.6 cm diameter, 0.5 μm pore size). The carbon dioxide outlet was located approximately 8 cm above the filter. The duration of the experiment was 260 minutes. FIGS. 2 and 3 are particles collected on the glass slide's up side (facing the nozzle). FIGS. 4 and 5 are particles collected on the filter.

EXAMPLE 2

Figure 6:
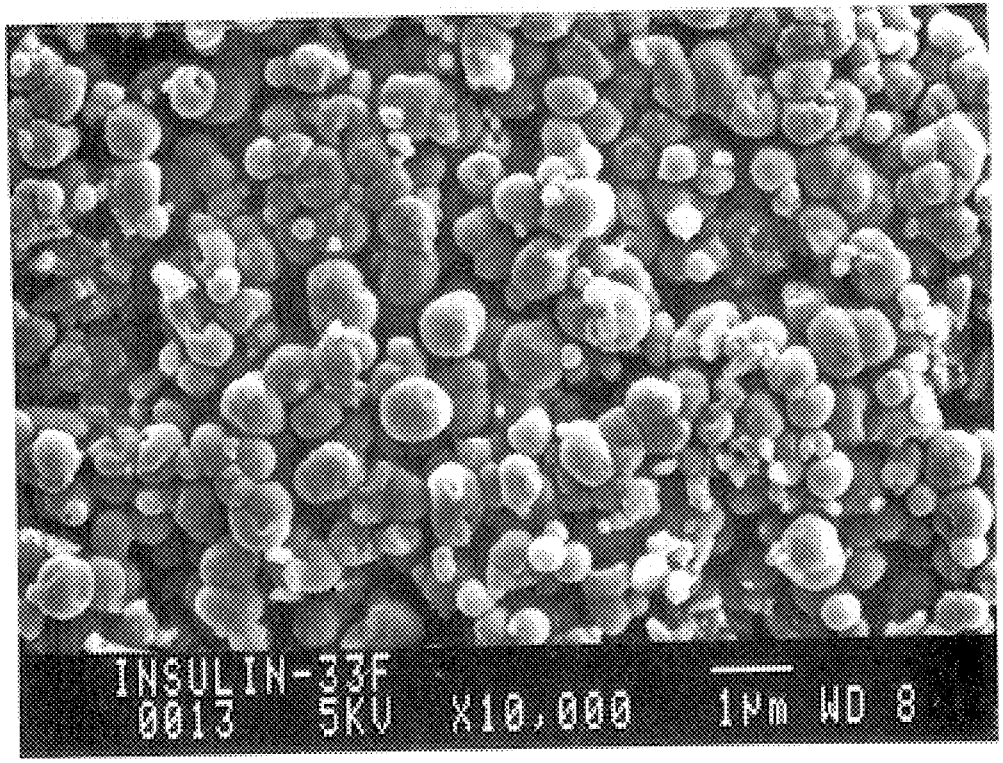
FIG. 6 is a microphotograph of the insulin particles made according to Example 2 magnified 10,000 times and collected on a filter.
Figure 7:
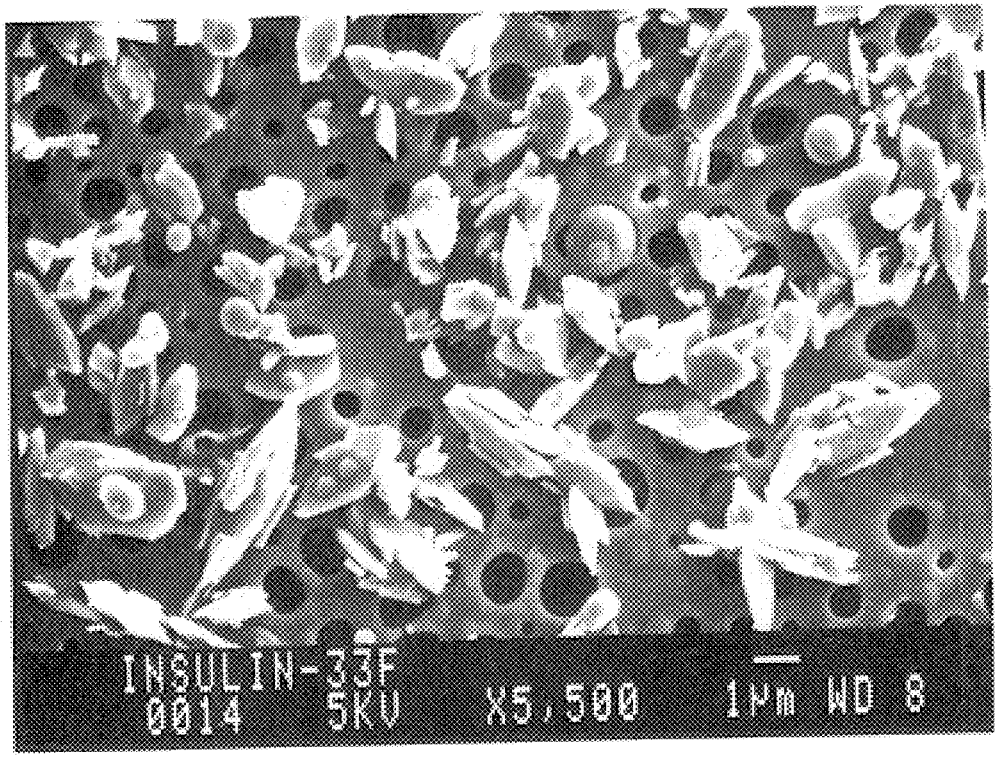
FIG. 7 is a microphotograph of insulin particles made in Example 2 magnified 5,500 times and collected on a filter.

Insulin particles, as shown in FIGS. 6 and 7, were made.

Liquid solution was used which had 20 mg zinc insulin [Miles; low endotoxin 86-003] in 200 ml of 90% ethanol (Pharmco Products Co., 200 proof)–10% water (deionized through a reverse osmosis apparatus, Hydro Picosystem) the solution pH was adjusted to 2.56 with HCl.

Liquid carbon dioxide (MG industries; Bone-dry grade, >99.8%) was compressed by a high pressure liquid pump 40. The delivery pressure (2000 psi) was controlled by a back-pressure regulator 42. The pressurized liquid was pre-heated to a supercritical temperature (35° C.) as it flowed through coiled tube 48 before entering the crystallizer 10. The system was enclosed, and thermostatting was achieved by circulating hot air under temperature control (Omega Engineering Model CN9000), with heating provided by strip heaters. The see-through crystallizer chamber 20 was kept at 35° C.

The supercritical fluid was fed to the crystallizer through a micrometering valve 46, with valves 1 and 4 open; and 2 and 3 closed. The pressure inside the crystallizer was kept at 1300 psi by back-pressure regulator 56. The instantaneous and total flow rates of supercritical fluid were measured with a rotameter 60 and dry test meter 62, respectively. The flow rate of the supercritical fluid was 35.6 g/min.

The liquid solution containing the enzyme was pressurized and circulated by liquid pump 32 under back-pressure regulator 34 control (1450 psi). The solution circulated through coil 36 and was preheated to 35° C. It entered the top of the crystallizer through a laser-drilled platinum disc (Ted Pella; 3 mm OD×0.24 mm thick; 20 μm), and emerged as very small droplets. The liquid flow rate was 0.39 cc/min. The liquid and supercritical streams circulated cocurrently downwards.

The fluid mixture of carbon dioxide and water exiting the crystallizer was depressurized and expanded to atmospheric pressure by flowing through cylindrical depressurizing tank 22 and a back-pressure regulator 58.

The supercritical fluid expanded and eventually dissolved most of the liquid solvent, causing the enzyme particles to precipitate. The particles were collected on an inclined glass slide located at the bottom of the crystallizer, forming an angle of approximately 10° to the direction of the protein solution's flow. Particles were also collected on a filter (Mott Metallurgical; 316 Stainless Steel, 1.6 cm diameter, 0.5 μm pore size). The carbon dioxide outlet was located approximately 60 mm below the filter.

The duration of the experiment was 296 minutes for carbon dioxide input, and 237 minutes for liquid input, followed by 17 minutes of liquid solution flow without dissolved enzyme.

FIGS. 6 illustrates particles collected on the filter which were needlelike having a diameter of less than 1 μm and a length of less than 3 μm. FIG. 7 illustrates particles collected which were globular, having an equivalent diameter of less than about 1 μm.

While exemplary embodiments of this invention have been described, the true scope of the invention is determined from the following claims.

What is claimed is:

1. A method of forming dry protein particles having an equivalent diameter of less than 5 μm with a narrow particle distribution which comprises bringing droplets of a liquid solution of the protein in a solvent for said protein, the droplets having diameters of from 10 μm to 500 μm, into contact at a controlled rate with an excess of a supercritical antisolvent having low solvent power for said protein but operable to dissolve in and expand said liquid solution and precipitate the dry protein particles.

2. The method according to claim 1 wherein the supercritical antisolvent is carbon dioxide, ethane, ethylene, sulfur hexafluoride, nitrous oxide, chlorotrifluoromethane, monofluoromethane, or mixtures thereof.

3. The method according to claim 2 wherein the supercritical antisolvent is carbon dioxide.

4. The method according to claim 1 wherein the solvent for the protein is ethanol, dimethylsulfoxide, tetrahydrofuran, acetic acid, formamide, N,N-dimethylformamide, ethylene glycol, liquid polyethylene glycol, or N,N-dimethylaniline.

5. The method according to claim 4 wherein the solvent for the protein is aqueous ethanol.

6. The method according to claim 1 wherein the solution of the protein is sprayed into a continuum of said supercritical antisolvent.

7. The method according to claim 1 wherein the protein has low water solubility.

8. The method according to claim 1 wherein the protein is insulin, catalase, adrenocorticotrophin hormone, or peroxidase.

9. A method of forming dry protein particles having an equivalent diameter of less than 5 μm with a narrow particle distribution which comprises bringing droplets of a liquid solution of the protein in a solvent for said protein, the droplets having diameters of from 10 μm to 500 μm, into contact at a controlled rate without change in pressure with an excess of a supercritical antisolvent having low solvent power for said protein but operable to dissolve in and expand said liquid solution and precipitate the dry protein particles.

* * * * *